United States Patent [19]

Langer, Jr. et al.

[11] 4,341,869
[45] Jul. 27, 1982

[54] PROCESS FOR PRODUCING HEPARINASE

[75] Inventors: Robert S. Langer, Jr., Cambridge; Robert Linhardt, Somerville; Charles L. Cooney, Brookline; Parrish M. Galliher, West Newton, all of Mass.

[73] Assignee: Massachusetts Institute of Technology, Cambridge, Mass.

[21] Appl. No.: 180,780

[22] Filed: Aug. 25, 1980

[51] Int. Cl.$^3$ .............................................. C12N 9/88
[52] U.S. Cl. .................................. 435/232; 435/815; 435/850
[58] Field of Search ............... 435/232, 850, 815, 200, 435/201

[56] References Cited
U.S. PATENT DOCUMENTS 3,549,500 12/1970 Suzuki .................................. 435/232

OTHER PUBLICATIONS

Applied and Environmental Microbiology, vol. 41, pp. 360–365, (Feb. 1981).
Linker et al. in Methods in Enzymology, vol. 28, pp. 902–911, (1972).
Hovingh et al. in The Journal of Biological Chemistry, vol. 245, No. 22, pp. 6170–6175, (Nov. 25, 1976).

Primary Examiner—Lionel M. Shapiro
Attorney, Agent, or Firm—Arthur A. Smith, Jr.; Paul J. Cook

[57] ABSTRACT

Heparinase is produced by growing the bacteria, *Flavobacterium heparinum*, in a defined medium consisting of a carbon source, two or more amino acids and mineral salts in the absence of protein. Heparinase is recovered by batch chromatography of the cell extract from hydroxylapatite by elution with sodium chloride and sodium phosphate buffer washes.

4 Claims, No Drawings

PROCESS FOR PRODUCING HEPARINASE

The Government has rights in this invention pursuant to Grant Number NIH-5-R01-GM25810-02 awarded by the Department of Health, Education and Welfare, National Institutes of Health.

BACKGROUND OF THE INVENTION

This invention relates to a process for producing heparinase utilizing a defined medium followed by a purification step.

Heparinase is an enzyme presently used in assays for heparin. Presently, heparinase is produced from *Flavobacterium heparinum* utilizing protein as the carbon, and nitrogen source and a phosphate source. In addition, presently available processes for producing heparinase provide a volumetric productivity of heparinase of about 1.8 mg heparin degrade/liter culture—hour. Furthermore, these prior processes require six stages of production including: (1) 72 hour fermentation; (2) Harvest by centrifugation; (3) 24 hour fermentation; (4) Harvest by centrifugation; (5) 17 hour incubation and (6) Harvest and sonication. In present processes, the crude enzyme produced by the bacterium is isolated by a step which includes passage of the crude enzyme through a column of hydroxylapatite $(Ca_x)(PO_4)y)$. It has been found that the heparinase binds more tightly to the hydroxylapatite than 90% of the protein present in *Flavobacterium heparinum*. Thus, a hydroxylapatite column can provide for 10-100 fold enzyme enrichment when the protein is eluted from th column at high eluent salt concentrations. However, hydroxylapatite is fragile and has poor flow characteristics in large columns and thus is not amenable to purification of much more than 1-10 grams of crude enzyme. Furthermore, each such purification requires nearly a week's time.

Accordingly, it would be desirable to provide a process for purifying heparinase which is not limited by the materials and methods utilized in purifying heparinase and which require far less time than required by present available processes. In addition, it would be desirable to provide such a process which drastically increases the volumetric productivity of heparinase.

SUMMARY OF THE INVENTION

In accordance with this invention, a process for producing heparinase is provided wherein the growth medium is a chemically defined medium comprised of a carbon source, a nitrogen source, a phosphate source, a magnesium source and a heparinase inducer in the absence of a chemically non-defined substances normally present in growth medium including a protein digest or yeast extract. Furthermore, in accordance with this invention, the product is purified in a batch process wherein the cell pellet is disrupted such as sonically, homogenization, enzyme treatment, osmotic shock, etc. The resultant extract then is mixed with hydroxylapatite followed by isolation of the heparinase bound to the hydroxylapatite utilizing an eluent comprised of phosphate buffer and sodium chloride in a stepwise fashion of increasing concentration of salt element such as sodium chloride, sodium phosphate, sodium acetate, the corresponding potassium salts or mixture thereof. A typical elution schedule is as follows:

(1) 0.01 M Sodium Phosphate pH 6.8
(2) 0.02 M Sodium Phosphate 0.03 M Sodium Chloride pH 6.8
(3) 0.04 M Sodium Phosphate 0.06 M Sodium Chloride pH 6.8
(4) 0.55 M Sodium Phosphate 0.09 M Sodium Chloride pH 6.8
(5) 0.07 M Sodium Phosphate 0.125 M Sodium Chloride pH 6.8
(6) 0.085 M Sodium Phosphate 0.16 M Sodium Chloride pH 6.8
(7) 0.10 M Sodium Phosphate 0.19 M Sodium Chloride pH 6.8

By utilizing this procedure, heparinase can be recovered from the 5th wash in as little a time as 8 hours with a specific activity of 80 mg heparin degraded/mg protein-hour. Accordingly, the present invention provides substantial efficiency and productivity for producing heparinase as compared to presently available processes.

DESCRIPTION OF SPECIFIC EMBODIMENTS

The strain of bacterium utilized in the present invention comprises *Flavobacterium heparinum* such as *Flavobacterium heparinum* ATCC 13125 or a mutant form of this bacterium.

The bacterium utilized in the present invention is grown in a chemically defined growth medium, i.e., a growth medium devoid of proteins, yeast extract or complex nutrients which are difficult to characterize and/or which vary in characteristics depending upon their source. The carbon source which can be utilized in the growth medium can comprise glucose, glycerol, maltose or heparin at concentrations for example of between about 0 g/l and about 20 g/l, usually between about 5 g/l and about 10 g/l. It is preferred to utilize glucose as the carbon source at a concentration of between about 5 g/l and about 10 g/l because of low cost.

In addition, the growth medium contains a source of phosphate such as monobasic or dibasic potassium phosphate, sodium mono or dibasic phosphate, ammonium phosphate or mixtures thereof. The growth medium also includes a source of nitrogen such as ammonium sulfate, heparin or amino acids and a source of magnesium such as magnesium sulfate, magnesium chloride or magnesium phosphate. The growth medium may also include a heparinase inducer comprising sodium heparin, heparin monosulfate, hyaluronic acid, maltose, N-acetyl, D-glucosamine or the like. Certain mutants of Flavobacterium heparinum need not require a heparinase inducer. A typical growth medium contains glucose, ammonium sulfate, and a mixture of potassium monobasic phosphate and sodium dibasic phosphate, magnesium sulfate, trace salts, L-methionine and L-histidine and the heparinase inducer. The ammonium sulfate can comprise between about 0.5 g/l and about 10 g/l, preferably 2 g/l; the mixture of phosphate can comprise between about 1 g/l and about 12 g/l, preferably 5 g/l; the magnesium sulfate comprises between about 0.1 g/l and about 1 g/l preferably 0.5 g/l; and the heparinase inducer comprises between about 0.05 g/l and about 10 g/l preferably 1.0 g/l. Trace salts were comprised of $Na_2MoO_4$, $CoCl_2$, $MnSO_4$, $CuSO_4$, $FeSO_4$, $CaCl_2$ all at $1 \times 10^{-4}$ M. L-Histidine and L-methionine at 0.2-0.5 g/l.

The pH of the medium generally is maintained between about 6 and about 8, preferable about 7. It is preferred to control the pH at about 7 during the course of the fermentation by the addition of ammonium hydroxide or sodium hydroxide. Sterile air is sparged into the fermentor at a rate sufficient to meet the needs of the bacterium and typically between about 0.25 VVM and about 0.5 VVM. The dissolved oxygen is set between 0 and 100% typically at 50%. The growth medium is maintained at a temperature between about 15° C. and about 32° C., preferably between about 22° C. and about 25° C. Optionally, the growth medium can contain an antifoaming agent such as P-2000 manufactured by Dow Chemical Company at a concentration between about 0.1 ml/l and about 1 ml/l to control foaming. Also, alternatively, the growth medium can contain an amino acid or a mixture of defined amino acids such as L-histidine and L-methionine.

The crude product then is purified by admixture in a batch mode with hydroxylapatite wherein the hydroxylapatite comprises between about 5 weight percent and about 15 weight percent of the mixture. The mixture is stirred gently for a period of time between about 1 minute and about 5 minutes at a temperature between about 0° C. and about 10° C. in order to selectively immobilize the heparinase on the hydroxylapatite. The immobilized heparinase then is removed from the hydroxylapatite by wash with increasing salt concentrations such as with sodium chloride and sodium phosphate at pH 6.8. Generally, the enriched eluent fractions are those containing about 0.07 M sodium phosphate and 0.125 M sodium chloride or between about 0.055 M sodium phosphate, 0.09 M sodium chloride and about 0.085 M sodium phosphate, 0.16 M sodium chloride and at pH 6.8.

The following examples illustrate the present invention and are not intended to limit the same.

EXAMPLE I

Flavobacterium heparinum ATCC 13125 was grown in a 14 liter fermentor at a 23° C., pH 7.0 (controlled by ammonium hydroxide addition) and aerated at a rate of 0.5 VVM with dissolved oxygen maintained at 50% of air saturation. 10 liters of a culture medium comprised of 10 g/l glucose, 2 g/l $(NH_4)_2SO_4$, 2.5 g/l $KH_2PO_4$, 2.5 g/l $NaH_2PO_4$ 0.5 g/l $MgSO_4.7H_2O$, 1.0 g/l sodium heparin, 0.1 g/l P-2000 anti-foaming agent, 0.5 g/l L-histidine, 0.5 g/l L-methionine trace salts $10^{-4}$ M. After about 25 hours of growth, the cells were harvested, centrifuged at 12,000×G, resuspended in 0.01 M phosphate buffer pH 6.8, sonicated to release 90% of protein. To this 6.5 g protamine sulfate was added, after 1 h at 4° C. was centrifuged at 12,00×G. This supernate was diluted with $H_2O$ to 2 liters then were admixed with 250 g hydroxylapatite at a temperature of 4° C. and at a pH of 6.8. The mixture was stirred for about 5 minutes in order to substantially completely bind heparinase to the hydroxylapatite. The hydroxylapatite then was isolated from the mixture by centrifugation at 1000×G and the supernate was decanted from it. The heparinase was eluted by washing with sodium chloride and sodium phosphate washes (pH 6.8) from 0.05 M Na phosphate to 0.1 M Na phosphate, 0.19 M NaCl and recovering the eluent. The heparinase was concentrated in the eluent comprising 0.07 M Na phosphate and 0.125 M sodium chloride.

We claim:

1. In a process for producing purified heparinase by growing *Flavobacterium heparinum* in a growth medium until heparinase is formed, the improvement which comprises admixing an extract of the *Flavobacterium heparinum* containing heparinase intimately with between about 5 and 15 weight percent hydroxylapatite based upon the weight of the mixture to bind said heparinase to said hydroxylapatite, recovering said hydroxylapatite containing bound heparinase and, recovering said bound heparinase by elution and wherein said growth medium is free of protein and yeast extract.

2. The process of claim 1 wherein elution is effected with sodium phosphate and sodium chloride.

3. The process of claim 1 wherein said growth medium includes a carbon source, a phosphate source, a nitrogen source, a magnesium source, at least two amino acids, trace salts and a heparinase inducer in the absence of protein and yeast extract.

4. The process of claim 2 wherein said growth medium includes a carbon source, a phosphate source, a nitrogen source, at least two amino acids, trace salts and a heparinase inducer in the absence of protein and yeast extract.

* * * * *